United States Patent
Sun et al.

(10) Patent No.: US 9,505,671 B2
(45) Date of Patent: *Nov. 29, 2016

(54) RENEWABLE PARA-XYLENE FROM ACETIC ACID

(71) Applicants: WASHINGTON STATE UNIVERSITY, Pullman, WA (US); ARCHER DANIELS MIDLAND COMPANY, Decatur, IL (US)

(72) Inventors: Junming Sun, Pullman, WA (US); Changjun Liu, Pullman, WA (US); Yong Wang, Pullman, WA (US); Colin Smith, Pullman, WA (US); Kevin Martin, Mt. Zion, IL (US); Padmesh Venkitasubramanian, Forsyth, IL (US)

(73) Assignees: Washington State University; Archer Daniels Midland Company

( * ) Notice: Subject to any disclaimer, the term of this patent is extended or adjusted under 35 U.S.C. 154(b) by 371 days.

This patent is subject to a terminal disclaimer.

(21) Appl. No.: 14/060,217

(22) Filed: Oct. 22, 2013

(65) Prior Publication Data

US 2014/0121430 A1    May 1, 2014

Related U.S. Application Data

(60) Provisional application No. 61/737,312, filed on Dec. 14, 2012, provisional application No. 61/720,433, filed on Oct. 31, 2012.

(51) Int. Cl.
| | |
|---|---|
| *C07C 1/20* | (2006.01) |
| *C07C 1/207* | (2006.01) |
| *C07C 2/12* | (2006.01) |
| *C07C 5/327* | (2006.01) |
| *C07C 5/393* | (2006.01) |
| *C07C 5/48* | (2006.01) |

(52) U.S. Cl.
CPC ............... *C07C 1/2078* (2013.01); *C07C 2/12* (2013.01); *C07C 5/327* (2013.01); *C07C 5/393* (2013.01); *C07C 5/48* (2013.01); *C07C 2521/06* (2013.01); *C07C 2523/06* (2013.01); *C07C 2529/40* (2013.01)

(58) Field of Classification Search
CPC ....................................................... C07C 1/20
USPC ................................ 585/638, 639, 640, 641
See application file for complete search history.

(56) References Cited

U.S. PATENT DOCUMENTS 3,769,237 A * 10/1973 Ondrey ................... B01J 23/26
                                                                502/311

OTHER PUBLICATIONS

Vervecken M. et al. "Zeolite induced selectivity in the conversion of the lower aliphatic carboxylic acids." Chemical Reactions in Organic and Inorganic Constrained Systems, 95-114. 1986. Reidel Publishing Company.*

* cited by examiner

*Primary Examiner* — Sharon Pregler
(74) *Attorney, Agent, or Firm* — William B. Miller

(57) ABSTRACT

A process is described for making renewable para-xylene, comprising converting acetic acid to isobutene in the presence of a catalyst then converting the acetic acid-derived isobutene to a product composition including para-xylene. The catalyst can be a $Zn_xZr_yO_z$ mixed oxide catalyst.

14 Claims, 1 Drawing Sheet

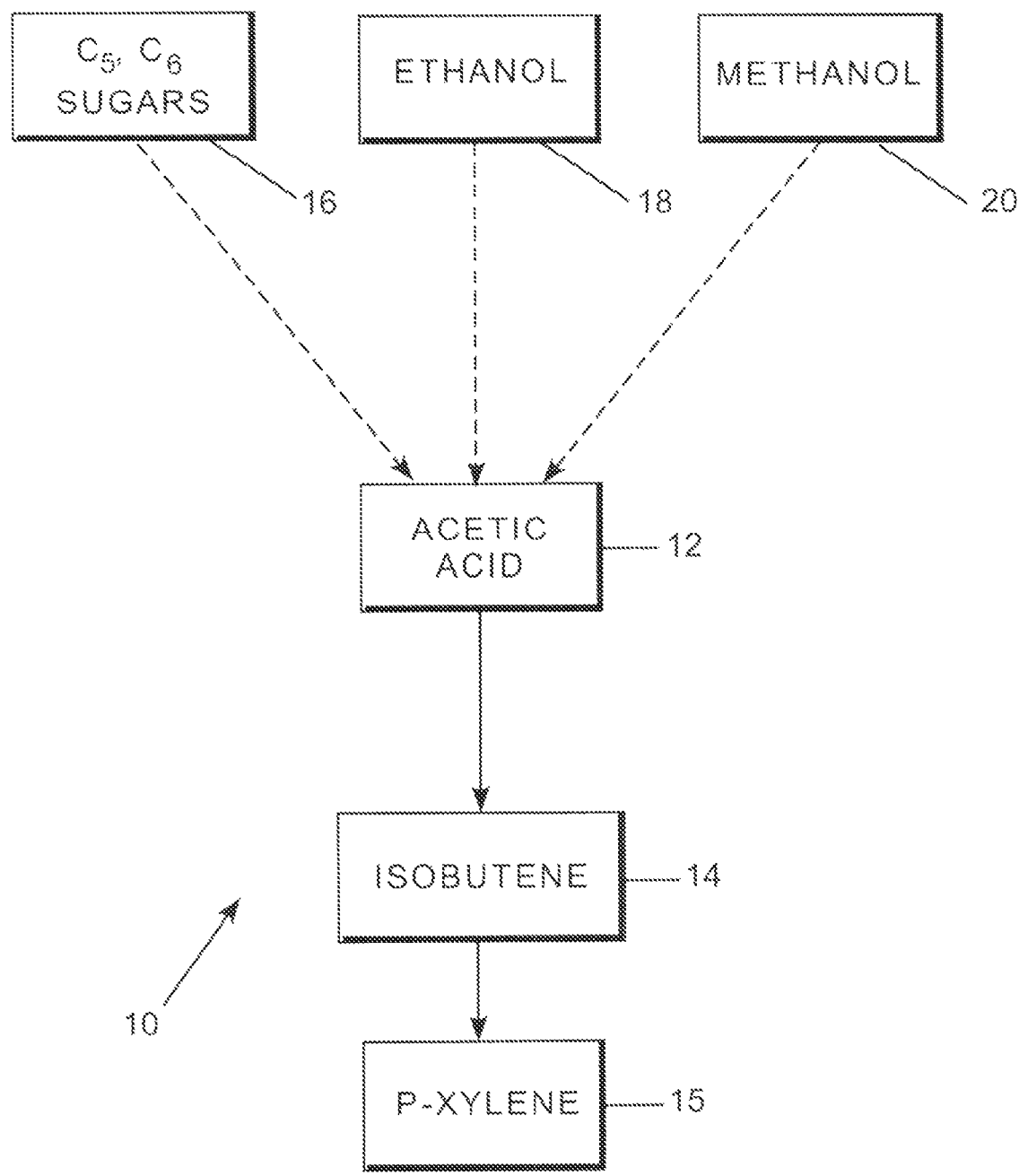

RENEWABLE PARA-XYLENE FROM ACETIC ACID

CROSS-REFERENCE TO RELATED APPLICATIONS

This application is a continuation-in-part of U.S. Patent Application Ser. No. 61/737,312 (the "'312 application"), filed Dec. 14, 2012 for "Process and Catalyst for Conversion of Acetic Acid to isobutene", which in turn was filed as a continuation-in-part of U.S. Patent Application Ser. No. 61/720,433 (the "'433 application), filed Oct. 31, 2012 for "Stable Mixed Oxide Catalysis for Direct Conversion of Ethanol to Isobutene and Process for Making". Both prior applications are accordingly hereby incorporated by reference.

BACKGROUND

US Patent Application Publication No. 2012/0271082 to Taylor et al., for "Variations on Prins-Like Chemistry to Produce 2,5-Dimethylhexadiene from Isobutanol" (hereafter, "Taylor et. al"), describes a method to produce 2,5-dimethylhexadiene from renewable isobutanol, from which in turn a renewable p-xylene (and subsequently, a renewable terephthalic acid, a key monomer in the production of PET) can be prepared. In addition, methods and catalysts are provided for producing 2,5-dimethylhexadiene from a variety of feed stocks that can act as "equivalents" of isobutylene and/or isobutyraldehyde including isobutanol, isobutylene oxide, and isobutyl ethers and acetals.

As background for the need of a source of renewable p-xylene, as summarized in Taylor et al., conventionally aromatic compounds such as para-xylene are produced from petroleum feedstocks in refineries by reacting mixtures of light hydrocarbons ($C_1$-$C_6$) and naphthas over various catalysts at high heat and pressure. The mixture of light hydrocarbons available to a refinery is diverse, and correspondingly provides a diverse mixture of aromatic compounds (e.g., BTEX benzene, toluene, ethylbenzene and xylenes, as well, as aromatic compounds having a molecular weight higher than xylenes). The xylenes product consists of three different aromatic $C_8$ isomers: p-xylene, o-xylene, and m-xylene; typically about one third of the xylenes are the p-xylene isomer. The BTEX mixture is then subjected to subsequent processes to obtain the desired product. For example, toluene can be removed and disproportionated to form benzene and xylene, or the individual xylene isomers can be isolated by fractionation (e.g. by absorptive separation, fractional crystallization, etc.). Para-xylene is the most commercially important xylene isomer, and is used almost exclusively in the production of polyester fibers, resins, and films.

Alternatively, a single component feedstock purified from crude oil or synthetically prepared at the refinery can be selectively converted to a purer aromatic product. For example, pure isooctene can be selectively aromatized to form primarily p-xylene over some catalysts (see, for example, U.S. Pat. No. 3,202,725, U.S. Pat. No. 4,229,320, U.S. Pat. No. 4,247,726, U.S. Pat. No. 6,600,081, and U.S. Pat. No. 7,067,708), and n-octane purified from crude oil can be converted to primarily o-xylene (see for example, U.S. Pat. No. 2,785,209).

Very high p-xylene purity is required to prepare terephthalic acid of suitable purity for use in polyester production; typically at least about 95% purity, or in some cases 99.7% or higher purity of p-xylene is required. Conventional, processes for producing high purity p-xylene are thus complex and expensive: the conventional BTEX process requires isolation and extensive purification of p-xylene produced at relatively low levels; and alternative processes require isolation, and purification of single component feedstocks for aromatization from complex hydrocarbon mixtures. Furthermore, production of p-xylene from conventional petroleum-based feedstocks contributes to environmental degradation (e.g., global warming, air and water pollution, etc.), and fosters over-dependence on unreliable petroleum supplies from politically unstable parts of the world.

Taylor et al. acknowledges that it had previously been known that p-xylene can also be made from 2,5-dimethyl-2,4-hexadiene in a high yielding, clean reaction over chromia and other metal oxide catalysts (citing U.S. patent application Ser. No. 12/986,918 filed Jan. 7, 2011, now published as U.S. Pat. No. 8,450,543). It had also been earlier established that the 2,5-dimethyl-2,4-hexadiene could in turn be prepared by combining isobutene (or t-butanol, or a combination of isobutene and t-butanol) with isobutyraldehyde over a niobic oxide catalyst under acidic conditions, for example as taught in U.S. Pat. No. 4,684,758. The isobutene could be renewably sourced, obtained either from dehydrating isobutanol or from ethanol from biomass fermentation methods, an example method for producing isobutene from ethanol being described in Sun et al., "Direct Conversion of Bio-ethanol to Isobutene on Nanosized $Zn_xZr_yO_z$ Mixed Oxides with Balanced Acid-Base Sites", Journal, of the American Chemical Society, vol. 133, pp. 11096-11099 (2011). Unfortunately, however, the process of the '758 patent was said by Taylor et al. to require a discrete isobutyraldehyde feed prepared from other, non-renewable source starting materials such as propylene and formaldehyde, so that the "overall process entails multiple processing steps from multiple, different raw materials."

Taylor et al. thus principally concerns methods for producing both of isobutylene (or isobutylene equivalents, e.g., isobutanol) and isobutyraldehyde (or isobutyraldehyde equivalents, e.g., isobutylene oxide) from isobutanol, and especially from renewable isobutanol, either in separate reactions or in situ with an olefin-aldehyde condensation reaction to form 2,5-dimethylhexadiene and/or 2-methyl-2,4-heptadiene. These synthons can then be coupled to form the desired dienes, which can then be cyclized to form o- and p-xylene. In certain favored embodiments, renewable isobutanol is the sole input chemical and is reacted under appropriate conditions to provide a product stream containing a desired fraction of isobutyraldehyde, e.g., via careful selection of oxidation catalysts and process conditions, and the partially oxidized product stream can then be reacted directly, eliminating the need for multiple feedstocks from both renewable and non-renewable sources.

At least one remaining difficulty with Taylor et al's approach, however, is that while a biosynthetic pathway to produce isobutanol has been known for some time using bacteria from the genus *Clostridium*, and while this pathway has been genetically engineered into a number of species of microorganisms more easily manipulated than those of the genus *Clostridium*, nevertheless, these engineered microorganisms had not achieved the ability to produce isobutanol in quantities large enough for commercial use. Peralta-Yahya, Pamela P.; Zhang, Fuzhong; del Cardayre, Stephen B.; Keasling, Jay D., "Microbial engineering for the production of advanced biofuels", *Nature*, vol. 488 (7411): 320-328 (15 Aug. 2012).

A somewhat earlier published application to the same assignee and naming some of the same inventors, US 2011/0087000 to Peters et al. (hereafter, "Peters et al."), is similarly directed to the production of renewable and relatively high purify p-xylene from biomass. The biomass is again treated to provide a fermentation feedstock and the fermentation feedstock then fermented with a microorganism for producing a $C_4$ alcohol such as the aforementioned isobutanol. The isobutanol is then sequentially dehydrated in the presence of a dehydration catalyst to provide a $C_4$ alkene such as isobutene. The $C_4$ alkene is dimerized to form one or more $C_8$ alkenes such as 2,4,4-trimethylpentenes or 2,5-dimethylhexene, then these materials are dehydrocyclized in the presence of a suitable dehydrocyclization catalyst to selectively form renewable p-xylene in high overall yield. The renewable p-xylene can then be oxidized to form terephthalic acid or terephthalate esters. Consequently, while the process steps in Peters et al. differ substantially from those in Taylor et al., nevertheless both are reliant on the same base technology for producing isobutanol by engineered microorganisms through fermentation.

It would, accordingly be advantageous if a process were available for making a renewable para-xylene that ultimately draws from a renewable feedstock that is already ubiquitous and inexpensive, and it would be particularly advantageous if this renewable feedstock also lent itself to the existing, known pathways to para-xylene from fossil fuel-based materials. We have now developed such a process.

SUMMARY OF THE PRESENT INVENTION

Accordingly, in a first aspect, the present invention concerns a process for making para-xylene, comprising converting acetic acid to isobutene in the presence of a catalyst, then converting the acetic acid-derived isobutene to a product composition including para-xylene.

In a first embodiment, the acetic acid-derived isobutene is oxidized to form a product composition including para-xylene.

In a second embodiment, the acetic-acid derived isobutene is converted to a product composition including para-xylene by first dimerizing acetic acid-derived isobutene in the presence of an oligomerization catalyst to form a dimerization product comprising one or more $C_8$ alkenes, then dehydrocyilzing at least a portion of the $C_8$ alkenes in the presence of a dehydrocyclization catalyst to form a product composition including para-xylene.

In preferred instances, para-xylene is produced selectively compared to its ortho- and meta-xylene isomers in the product composition.

The present invention stems from the discovery, described more completely in the incorporated '312 application, that the mixed oxide catalysts we have been evaluating for converting ethanol to isobutene (including but not being limited to the more stable catalysts described in the incorporated '433 application) are also able to catalyze the conversion of acetic acid to isobutene. Since acetic acid can be made by a variety of methods from a number of different starting materials, including through carbonylation of methanol derived from sequestered carbon dioxide, for example, the capability of these mixed oxide catalysts to catalyze the conversion of acetic acid to isobutene enables a number of improvements to be realized and a range of options for utilizing renewable resources more efficiently, all as described in greater detail hereafter. Moreover, as already mentioned apart from a consideration of these options, acetic acid as a starting material offers the advantages of already being widely available from established methods and sources.

BRIEF DESCRIPTION OF THE DRAWING

FIG. 1 schematically depicts a process of converting acetic acid to isobutene in the presence of a catalyst and subsequently converting the isobutene to p-xylene, wherein various options for obtaining the acetic acid are suggested.

DETAILED DESCRIPTION

Referring now to FIG. 1, a process 10 is schematically illustrated wherein acetic acid 12 is converted to isobutene 14 in the presence of a catalyst, particularly, a $Zn_xZr_yO_z$ mixed oxide catalyst, and the isobutene 14 is subsequently converted to a product composition including p-xylene 15.

Considering first the conversion of acetic acid 12 to isobutene 14, according to a first embodiment, a $Zn_xZr_yO_z$ mixed oxide catalyst useful for that conversion can be made by a "hard template" or "confined space synthesis" method generally of the character used by Jacobsen et al., "Mesoporous Zeolite Single Crystals", Journal of the American Chemical Society, vol. 122, pp. 7116-7117 (2000), wherein nanozeolites were prepared.

More particularly, the same carbon black (BP 2000, Cabot Corp.) may be used as a hard template for the synthesis of nanosized $Zn_xZr_yO_z$ mixed oxides, rather than nanozeolites as in Jacobsen et al. Prior to use, the BP 2000 template is dried, for example, at 180° C. overnight. Calculated amounts of zirconyl nitrate hydrate (Sigma-Aldrich, greater than 99.8% purity) and $Zn(NO_3)_2 \cdot 6H_2O$ (Sigma-Aldrich, greater than 99.8% purity) are dissolved in a given amount of water, and sonicated for 15 minutes to produce a clear solution with desired concentrations of Zn and Zr. In one preparation, about 25 grams of the obtained solution are then mixed with 6.0 grams of the preheated BP 2000 to achieve incipient wetness, and the mixture is transferred to a ceramic crucible and calcined at 400 degrees Celsius for 4 hours, followed by ramping the temperature to 550 degrees Celsius (at a ramp rate of 3 degrees Celsius/minute) and holding at 550 degrees Celsius for another 20 hours. Nanosized white powders are obtained, having a mean particle size of less than 10 nanometers.

The nanosized $Zn_xZr_yC_z$ mixed oxide catalysts made by a hard template method are further described in Sun et al, "Direct Conversion of Bio-ethanol to Isobutene on Nanosized $Zn_xZr_yO_z$ Mixed Oxides with Balanced Acid-Base Sites", Journal of the American Chemical Society, vol. 133, pp. 11096-11099 (2011), along with findings related to the character of the mixed oxide catalysts formed thereby and the performance of the catalysts for the ethanol to isobutene conversion, given certain Zn/Zr ratios, residence times and reaction temperatures.

Alternatively, the $Zn_xZr_yO_z$ mixed oxide catalysts may be made as described in copending U.S. Patent Application Ser. No. 61/720,433, filed Oct. 31, 2012 for "Stable Mixed Oxide Catalysts for Direct Conversion, of Ethanol to Isobutene and Process for Making" (the '433 application), by a process broadly comprising, in certain embodiments, forming a solution of one or more Zn compounds, combining one or more zirconium-containing solids with the solution of one or more Zn compounds so that the solution wets the zirconium-containing solids to a state of incipient wetness, drying the wetted solids, then calcining the dried solids. In other embodiments, a solution is formed of one or more Zr compounds, the solution is combined with one or more Zn-containing solids so that the solution wets the Zn-containing solids to a state of incipient wetness, the wetted solids are dried and then the dried solids are calcined.

In certain embodiments, the $Zn_xZr_yO_z$ mixed oxide catalysts (whether made by the hard template or incipient wetness methods) are characterized by a Zn/Zr ratio (x:y) of from about 1:1.00 to about 10:1, preferably from about 1:30 to about 1:1, especially about 1:20 to about 1:5, and still more preferably about 1:12 to about 1:10.

The catalysts made by the alternative, incipient wetness method are consistent in their particle size with the catalysts described in the incorporated journal article, namely, comprising aggregates of less than 10 nm-sized particles with a highly crystalline structure. The Zn oxide component is again highly dispersed on the Zr oxide component.

In certain embodiments, the $Zn_xZr_yO_z$ mixed oxide catalysts are characterized as low sulfur catalysts, containing less than about 0.14 percent by weight of sulfur. In the '433 application, it was reported in this regard that catalysts made by the incipient wetness method would desirably be substantially sulfur-free, preferably including less than about 0.01 percent by weight of sulfur and more preferably including less than about 0.001 weight percent of sulfur. In the '433 application, it was postulated that the reduced sulfur content enabled by the incipient wetness method as compared to the hard template method contributed significantly to the much improved stability observed for the incipient wetness method catalysts of the prior related application for the ethanol to isobutene process.

In converting acetic acid to isobutene, however, in at least some embodiments and under certain process conditions some sulfur does appear to be beneficial, though as just indicated. It is expected that the amount of sulfur will preferably be such that the catalysts are characterized as low sulfur catalysts. Such low sulfur catalysts are most readily made by the incipient wetness method described briefly above and in greater detail in the '433 application.

In principle, provided the zinc and zirconium compounds and solids in these embodiments have a sufficiently low sulfur content in order to produce a low sulfur content when combined according to the incipient wetness method, any combination of zinc and zirconium materials and any solvent can be used that will permit the zinc and zirconium components to mix homogeneously whereby, through incipient wetness impregnation, one of the zinc or zirconium components are well dispersed on a solid of the other component for subsequent drying and conversion to the oxide forms through calcining. Low sulfur catalysts can also be made by the incipient wetness method starting with zinc and zirconium compounds that are sulfur-free or substantially sulfur-free, then doping in a desired sulfur content into the $Zn_xZr_yO_z$ mixed oxide catalysts.

The conditions and times for the drying and calcining steps of an incipient wetness preparation will depend, of course, on the particular zinc and zirconium materials and solvent used, but in general terms, the drying step can be accomplished in a temperature range of from about 60 degrees Celsius to about 200 degrees Celsius over at least about 3 hours, while the calcining can take place at a temperature of from about 300 degrees Celsius to about 1500 degrees Celsius, but more preferably a temperature of from about 400 to 600 degrees Celsius is used. The calcination time can be from about 10 minutes to about 48 hours, with from about 2 to about 10 hours being preferred.

In still other embodiments, low sulfur catalysts could be prepared by a hard template method, except that a suitably very low sulfur content carbon is used for the hard template to realize a low sulfur content in the finished catalyst.

In certain embodiments, the acetic acid, to isobutene conversion can be accomplished continuously in the gas phase, using a fixed bed reactor or flow bed reactor. The reaction temperature may be in a range from about 350 to about 700 degrees Celsius, preferably, in a range from about 400 to about 500 degrees Celsius, and the WHSV can be in a range from about 0.01 $hr^{-1}$ to about 10 $hr^{-1}$, preferably from about 0.05 $hr^{-1}$ to about 2 $hr^{-1}$. Acetic acid/water solutions with steam, to carbon ratios from 0 to 20, preferably from 2 to 5 can be used to provide acetic acid to the catalyst. An inert carrier gas, such as nitrogen, can be used.

As shown schematically in FIG. 1, the acetic acid 12 for the first acetic acid to isobutene step can be obtained by various methods from a number of starting materials, which in turn permits a number of integrated processes to be considered for producing other products in addition to isobutene and/or for providing improved utilization of renewable resources.

For example, acetic acid can be produced from a source of five and six carbon sugars 16 by fermentation. U.S. Pat. No. 6,509,180 and U.S. Pat. No. 8,252,567 seek to improve upon known processes for making ethanol and butanol/hexanol, respectively, by means including the fermentation of five and six carbon sugars into acetic acid. In U.S. Pat. No. 6,509,180, the acetic acid is esterified to form an acetate ester which may then be hydrogenated (using hydrogen from, e.g., steam reforming of natural gas, electrolysis of water, gasification of biomass or partial oxidation of hydrocarbons generally) to ethanol. In U.S. Pat. No. 8,252,567, the ethanol formed in this manner can be used to make butanol and hexanol by subjecting the ethanol with acetate, acetic acid or mixtures thereof to an acidogenic fermentation using, for example, species of the bacteria *Clostridium* (*Clostridium kluyveri* is mentioned), to produce butyrate, butyric acid, caproate, caproic acid or mixtures thereof. These materials then in turn are acidified to convert butyrate and caproate to butyric acid and caproic acid, the butyric and caproic acids are esterified and then the butyric and caproic acid esters undergo reduction by hydrogenation, hydrogenolysis or reduction by carbon monoxide to provide butanol and ethanol.

As related in these two patents and as well known to those skilled in the fermentation art the fermentation of five and six carbon sugars to form acetic acid can be accomplished by various organisms. More particularly, homoacetogenic microorganisms are able through fermentation to produce acetic acid with 100% carbon yield; these microorganisms internally convert carbon dioxide to acetate, in contrast to a process for producing ethanol from sugars obtained from biomass (the starting point for isobutene syntheses reported in the prior related application and in the earlier journal article (Sun et al., "Direct Conversion of Bio-ethanol to Isobutene on Nanosized ZnxZryOz Mixed Oxides with Balanced Acid-Base Sites", Journal of the American Chemical Society, vol. 133, pp 11096-11099 (2011)) wherein carbon dioxide is produced as a byproduct.

Examples of homoacetogens given by U.S. Pat. No. 8,252,567 are microorganisms of the genus *Moorella* and *Clostridium*, especially microorganisms of the species *Moorella thermoaceticum* (described as formerly classified as *Clostridium thermoaceticum*) or *Clostridium formicoaceticum*, U.S. Pat. No. 8,252,567 represents that about one hundred known acetogens in twenty-two genera were known as of 2009, and cross-references Drake, et al., Ann. NY Acad. Sci. 1125: 100-128 (2008) for a review of acetogenic microorganisms.

Other references describing fermentation methods for producing acetic acid from five and six carbon sugars include U.S. Pat. No. 4,935,360; U.S. Pat. No. 8,236,534; U.S. Pat. No. 4,513,084; U.S. Pat. No. 4,371,619 and U.S. Pat. No. 4,506,012; both one-step fermentation processes from the sugars to acetic acid, acetates or both are disclosed, as well as two-step processes involving a first fermentation to lactic acid (by lactobacillus or known methods of homolactic fermentation, preferably) followed by a second fermentation to convert lactic acid to acetic acid, for example, using *Clostridium formicoaceticum*.

Any of the known, fermentation methods may, in short, be used to produce acetic acid for conversion to isobutene in the presence of the mixed oxide catalysts, but homoacetogenic fermentation methods are considered preferable in that carbon dioxide is not produced as a byproduct—the carbon dioxide represents a yield loss from the overall process to make isobutene and as a greenhouse gas is undesirable particularly in the context of a process to make a needed product more sustainably from renewable resources.

As well or in the alternative, the acetic acid feedstock 12 can be made from ethanol 18, according to any of several known methods employing oxidative fermentation with acetic acid bacteria of the genus *Acetobacter*.

As well or in the alternative, the acetic acid feedstock 12 can be made from methanol 20 through combination with carbon monoxide according to the most industrially used route for making acetic acid, for example, in the presence of a catalyst under conditions effective for the carbonylation of methanol. A variety of carbonylation catalysts are known in this regard, see, for example, U.S. Pat. No. 5,672,743; U.S. Pat. No. 5,728,871; U.S. Pat. No. 5,773,642; U.S. Pat. No. 5,883,289; U.S. Pat. No. 5,883,295.

Those skilled in the art will appreciate that making at least a portion of the acetic acid feedstock 12 from methanol 20 would enable other integrated process options to be considered for making isobutene and then p-xylene from a biomass. Thus, syngas may be produced by gasification of a biomass, and methanol then produced from the syngas with additional hydrogen provided, for example, through electrolysis of water. The electrical energy required for the electrolysis may in turn be generated from combustion of additional biomass, through steam from heat energy captured from the methanol synthesis or from combustion of a biomass fraction (lignin, for example), with optional capture and recycle of carbon dioxide from, the flue gas to be used in the methanol synthesis. A variety of options for producing methanol from, biomass have been presented in the literature, see, for example, US 2007/0254969 A1 by Olah et. al; U.S. Pat. No. 6,645,442 and U.S. Pat. No. 6,991,769, both by Kaneko et al; and U.S. Pat. No. 6,340,581 to Gaddy.

Those skilled in the art will appreciate that still other options may be considered for producing acetic acid from biomass or from a biomass fraction, including by catalytic, thermochemical and biological means, and that the limited description of various embodiments provided above should by no means be construed as limiting of the ways in which the acetic acid feedstock 12 may be made using renewable resources inclusive fundamentally of biomass, carbon monoxide and carbon dioxide gases. For example, as is known, the required acetic acid may be made at least in some part by anaerobic fermentation using carbon monoxide and carbon dioxide gases themselves for a carbon source.

Turning now to the conversion of the thusly-obtained isobutene 14 to a product composition including p-xylene 15, in one embodiment this is accomplished by dimerizing the isobutene 14 in the presence of an oligomerization catalyst, obtaining a dimerization product comprising one or more $C_8$ alkenes (optionally containing unreacted isobutene 14, and optionally comprising 2,4,4-trimethylpentenes, 2,5-dimethylhexene(s), and/or 2,5-dimethylhexadiene(s)), then dehydrocyclizing at least a portion of the $C_8$ alkene(s) in the dimerization product in the presence of a dehydrocyclization catalyst to provide a dehydrocyclization product composition including xylenes and hydrogen (and optionally including unreacted isobutene, 2,4,4-trimethylpentene(s), 2,5-dimethylhexene(s), and/or 2,5-dimethylhexadiene(s)). In certain embodiments, the isobutene 14 has been recovered or purified from other components in the product composition from the conversion of acetic acid 12 to isobutene 14 according to the '312 application, while in alternate embodiments, the dimerization can be performed on the product composition from the acetic acid to isobutene conversion step.

The "dimerization" or "dimerizing" refers to oligomerization processes in which two identical activated molecules (such as isobutene) are combined with the assistance of a catalyst (a dimerization catalyst or oligomerization catalyst, as described herein) to form, a larger molecule having twice the molecular weight of either of the starting molecules (such as diisobutene or 2,4,4-trimethylpentenes). The term "oligomerization" can equally be used to refer to a "dimerization" reaction, unless the formation of oligomers other than dimers is expressly or implicitly indicated.

"Dehydrocyclization" refers to a reaction in which an alkane or alkene is converted into an aromatic hydrocarbon and hydrogen, usually in the presence of a suitable dehydrocyclization catalyst, for example, any of those described herein.

The oligomerization catalyst catalyzes dimerization, trimerization, etc. of the isobutene. In the process of the present invention, primarily dimerization of the isobutene to $C_8$ alkene(s) (e.g., 2,4,4-trimethylpentenes, etc.) is favored by an appropriate selection of oligomerization catalyst and process conditions. In most embodiments, the dimerization reaction step is carried out under conditions which favor substantially exclusively the dimer product, that is, at least about 90% of the oligomers formed are $C_8$ alkene, preferably at least about 95% of the oligomers formed are $C_8$ alkene, more preferably at least about 98% of the oligomers formed are $C_8$ alkene, still more preferably at least about 99% of the oligomers are $C_8$ alkene and most preferably about 100% of the oligomers formed are $C_8$ alkene. Unreacted isobutene is then recycled.

Furthermore, the dimerization process is preferably carried under selective conditions so that the $C_8$ alkene formed comprises primarily 2,4,4-trimethylpentenes; that is, the $C_8$ alkene dimers comprise at least about 50% 2,4,4-trimethylpentenes, or at least about 55%, at least about 60%, at least about 65%, at least about 70%, at least about 75%, at least about 80%, at least about 85%, at least about 90%, at least about 95%, or about 100% of 2,4,4-trimethylpentenes.

In other embodiments, the dimerization process is carried under selective conditions so that the $C_8$ alkene formed comprises primarily 2,5-dimethylhexenes; that is, the $C_8$ alkene dimers comprise at least about 50% 2,5-dimethylhexenes, or at least about 55%, at least about 60%, at least about 65%, at least about 70%, at least about 75%, at least about 80%, at least about 85%, at least about 90%, at least about 95%, or about 100% 2,5-dimethylhexenes.

In still other embodiments, the dimerization process is carried under selective conditions so that the $C_8$ alkene formed comprises primarily 2,5-dimethylhexadienes; that is, the $C_8$ alkene dimers comprise at least about 50% 2,5-dimethylhexadienes, or at least about 55%, at least about 60%, at least about 65%, at least about 70%, at least about 75%, at least about 80%, at least about 85%, at least about 90%, at least about 95%, or about 100% 2,5-dimethylhexadienes.

In further embodiments, the dimerization process is carried under selective conditions so that the $C_8$ alkene formed comprises primarily 2,5-dimethylhexenes and 2,5-dimethylhexadienes; that is, the $C_8$ alkene dimers comprise at least about 50% 2,5-dimethylhexenes and 2,5-dimethylhexadienes, or at least about 55%, at least about 60%, at least about 65%, at least about 70%, at least about 75%, at least about 80%, at least about 85%, at least about 90%, at least about 95%, or about 100% 2,5-dimethylhexenes and 2,5-dimethyl-hexadienes.

At the high conversion conditions typical in petrochemical processing of the $C_8$ alkenes (e.g., >95% conversion), the oligomerization product typically comprises a mixture of isooctenes and isododecenes, which would require isolation and purification of the isooctene component prior to dehydrocyclizatlon in order to provide sufficiently pure p-xylene. The selective dimerization conditions as described herein provide high levels of diisobutylene, for example 2,4,4,-trimethylpentenes, 2,5-dimethylhexenes, or 2,5-dimethylhexadienes, which can be converted subsequently to substantially pure p-xylene by dehydrocyclization as described herein. Selective dimerization conditions which produce essentially exclusively dimer alkene product comprising at least about 50% 2,4,4-trimethylpentenes, 2,5-dimethylhexenes, or 2,5-dimethylhexadienes (or in other embodiments, at least about 55%, at least about 60%, at least about 65%, at least about 70%, at least about 73%, at least about 80%, at least about 85%, at least about 95%, at least about 95%, or about 100% 2,4,4-trimethylpentenes, 2,5-dimethylhexenes, or 2,5-dimethylhexadienes, inclusive of all ranges and subranges therebetween) are provided by various means, for example catalyst selection, choice of temperature and/or pressure, WHSV, the presence of diluents and modifiers, and combinations thereof. Suitable selective dimerization conditions include, for example, dimerization with an Amberlyst strongly acidic ionic exchange resin catalyst at a temperature of about 100-1200 degrees Celsius, approximately atmospheric pressure, a WHSV of about 10-50 $hr^{-1}$, and a feedstock comprising about 50-90% diluents; for a ZSM-5 zeolite catalyst (e.g. CBV 2314), suitable dimerization conditions include a reaction temperature of about 150-180 degrees Celsius, a pressure of about 750 psig, a WHSV of about 10-100 $hr^{-1}$, and a feedstock comprising about 30-90% diluents; and for a solid phosphoric acid catalyst, suitable conditions include a reaction temperature of about 160-190 degrees Celsius, a pressure of about 500-1000 psig, a WHSV of about 10-100 $hr^{-1}$ and a feedstock comprising about 25-75% diluents.

A non-limiting list of suitable acidic oligomerization catalysts includes inorganic acids, organic sulfonic acids, heteropolyacids, perfluoroalkyl sulfonic acids, metal salts thereof, mixtures of metal salts, and combinations thereof. The acid catalyst may also be selected from the group consisting of zeolites such as CBV-3020, ZSM-5, B Zeolite CP SMC, ZSM-5 CBV 8014, ZSM-5 CBV 5524 G, and YCBV 870; fluorinated alumina; acid-treated silica; acid-treated silica-alumina; acid-treated titania; acid-treated zirconia; heteropolyacids supported on zirconia, titania, alumina, silica; and combinations thereof. The acid catalyst may also be selected from the group consisting of metal sulfonates, metal sulfates, metal trifluoroacetates, metal inflates, and mixtures thereof; mixtures of salts with their conjugate acids, zinc tetrafluoroborate, and combinations thereof.

Other acid catalysts that may be employed in the dimerization step include inorganic acids such as sulfuric acid, phosphoric acid (e.g., solid phosphoric acid), hydrochloric acid, and nitric acid, as well as mixtures thereof. Organic acids such as p-toluene sulfonic acid, triflic acid, trifluoroacetic acid and methanesulfonic acid may also be used. Moreover, ion exchange resins in the acid form may also be employed. Hence, any type of suitable acid catalyst known, in the art may be employed.

Fluorinated sulfonic acid polymers can also be used as acidic oligomerization catalysts for the dimerization step. These acids are partially or totally fluorinated hydrocarbon polymers containing pendant sulfonic add groups, which may be partially or totally converted to the salt form. One suitable fluorinated sulfonic acid polymer is Nafion® perfluorinated sulfonic acid polymer (E.I. duPont de Nemours and Company, Wilmington, Del.). Another suitable fluorinated sulfonic acid polymer is Nafion® Super Acid Catalyst, a bead-form strongly acidic resin which, is a copolymer of tetrafluoroethylene and perfluoro-3,6-dioxa-4-methyl-7-octene sulfonyl fluoride, converted to either the proton (H+), or the metal salt form.

A soluble acidic oligomerization catalyst may also be used. Suitable soluble acids include, those acid catalysts with a pKa less than, about 4, preferably with a pKa less than about 2, including inorganic acids, organic sulfonic acids, heteropolyacids, perfluoroalkylsulfonic acids, and combinations thereof. Also suitable are metal salts of acids with a pKa less than about 4, including metal sulfonates, metal sulfates, metal trifluoroacetates, metal triflates, and mixtures thereof, including mixtures of salts with their conjugate acids. Specific examples of suitable acids include sulfuric acid, fluorosulfonic acid, phosphoric acid, p-toluenesulfonic acid, benzenesulfonic acid, phosphotungstic acid, phosphomolybdic acid, trifluoromethanesulfonic acid, 1,1,2,2-tetrafluoroethanesulfonic acid, 1,1,1,2,3,3-hexafluoropropanesulfonic acid, bismuth triflate, yttrium inflate, ytterbium Inflate, neodymium inflate, lanthanum triflate, scandium triflate, zirconium triflate, and zinc tetrafluoroborate.

For batch reactions, the acidic oligomerization catalyst is preferably used in an amount of from about 0.01% to about 50% by weight of the reactants (although the concentration of acid catalyst may exceed 50% for reactions run in continuous mode using a packed bed reactor). In a particular embodiment, the range is 0.25% to 5% by weight of the readmits unless the reaction is run in continuous mode using a packed bed reactor. For flow reactors, the acid catalyst will be present in amounts that provide WHSV values ranging from about 0.1 $hr^{-1}$ to 500 $hr^{-1}$ (e.g., about 0.1, about 0.5, about 1.0, about 2.0, about 5.0, about 10, about 20, about 30, about 40, about 50, about 60, about 70, about 80, about 90, about 100, about 150, about 200, about 250, about 300, about 350, about 400, about 450, or about 500 $hr^{-1}$).

Other suitable heterogeneous acid catalysts include, for example, acid treated clays, heterogeneous heteropolyacids and sulfated zirconia. The acid catalyst can also be selected from the group consisting of sulfuric acid-treated silica, sulfuric acid-treated silica-alumina, acid-treated titania, acid-treated zirconia, heteropolyacids supported on zirconia, heteropolyacids supported on titania, heteropolyacids supported on alumina, heteropolyacids supported on silica, and combinations thereof. Suitable heterogeneous acid catalysts include those having a Hammett acidity ($H_0$) of less than, or equal to 2.

In most embodiments, the dimerization step is typically carried out using a fixed-bed reactor using any of the oligomerization catalysts described herein. Alternatively, other types of reactors known in the art can be used, such as fluidized bed reactors, batch reactors, catalytic distillation reactors and so forth. In a particular embodiment, the oligomerization catalyst is an acidic catalyst such as ZSM-5, solid phosphoric acid catalyst or a sulfonic acid resin.

As discussed herein, higher selectivity for formation of dimers such as 2,4,4-trimethylpentenes, 2,5 dimethylhexenes, and 2,5-dimethylhexadienes is favored at lower conversion and under milder oligomerization conditions (e.g., lower temperature and pressure). In most embodiments, the reaction is carried out in the liquid phase at a pressure ranging from 0-1500 psig, and at a temperature of about 250° C. or less. In some embodiments, the oligomerization reaction pressure is about 0, about 15, about 30, about 45, about 60, about 75, about 90, about 105, about 120, about 135, about 150, about 165, about 180, about 195, about 210, about 225, about 240, about 255, about 270, about 285, about 300, about 350, about 400, about 450, about 500, about 550, about 600, about 650, about 700, about 750, about 800, about 850, about 900, about 950, about 1000, about 100, about 1200, about 1300, about 1400, or about 1500 psig, inclusive of all ranges and subranges therebetween.

In other embodiments, the dimerization reaction temperature is about 250° C. or less, about 225° C. or less, about 200° C. or less, about 175° C. or less, about 150° C. or less, about 125° C. or less, about 100° C. or less, about 75° C. or less, or about 50° C. or less, inclusive of all ranges and subranges therebetween, in a specific embodiment, the oligomerization temperature is about 170° C.

The weight hourly space velocity (WHSV) of the oligomerization reaction can range from about 1 $hr^{-1}$ to about 500 $hr^{-1}$ or about 1, about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 95, about 100, about 110, about 120, about 130, about 140, about 150, about 175, about 200, about 225, about 250, about 275, about 300, about 350, about 400, about 450, or about 500 $hr^{-1}$. In a specific embodiment, the WHSV is about 5 $hr^{-1}$.

The renewable $C_8$ alkenes prepared after the oligomerization step have three, two or at least one double bond. On average, the product of the oligomerizing step has less than about two double bonds per molecule, in particular embodiments, less than about 1.5 double bonds per molecule. In most embodiments, the Q alkenes have on average one double bond.

Selective dimerization of the acetic acid-derived isobutene during the dimerization step can also be promoted by the addition of alcohols such as t-butanol and diluents such as paraffins (such as kerosene, isooctane, or isobutane) to the oligomerization feedstock. In other embodiments, the selectivity of the dimerization reaction can be enhanced by adding water and isobutanol, e.g., by adding aqueous isobutanol.

Some rearrangement of the isobutene feedstock or $C_8$ alkene dimerization product may also occur, thereby introducing new or undesired branching patterns into the $C_8$ alkene products. In most embodiments, rearrangement of the isobutene feedstock and/or $C_8$ alkene product is not desirable so that the oligomerization reaction conditions and catalyst are preferably selected to minimize or eliminate such rearrangements (e.g., temperatures below about 200° C., or below about 180° C., and in particular embodiments, about 170° C.).

For the dehydrocyclization step, a variety of alumina and silica based catalysts and reactor configurations have been used to prepare aromatics from low molecular weight hydrocarbons. For example, a gallium-doped zeolite catalyst has been reported for converting liquefied petroleum gas into aromatic compounds, see *Appl. Catal, A*, no. 89, pp. 1-30 (1992). Other reported catalysts include bismuth, lead or antimony oxides (U.S. Pat. Nos. 3,644,550 and 3,830,866), chromium-treated alumina (U.S. Pat. Nos. 3,836,603 and 6,600,081), rhenium-treated alumina (U.S. Pat. No. 4,229,320) and platinum treated zeolites (WO 2005/065393 A2). A non-limiting list of such catalysts include: mixtures of chromia-alumina and bismuth oxide (e.g., bismuth oxide prepared by the thermal decomposition of bismuth compounds such as bismuth nitrate, bismuth carbonate, bismuth hydroxide, bismuth acetate, etc. and e.g., chromia-alumina prepared by impregnating alumina particles with a chromium composition to provide particles containing about 5, about 10, about 15, about 20, about 25, about 30, about 35, about 40, about 45, or about 50 mol % chromia, optionally including a promoter such as potassium, sodium, or silicon, and optionally including a diluent such as silicon carbide, alumina, zirconium oxide, etc.); bismuth oxide, lead oxide or antimony oxide in combination with supported platinum, supported palladium, supported cobalt, or a metal oxide or mixtures thereof, such as chromia-alumina, cobalt molybdate, tin oxide or zinc oxide; supported chromium, on a refractory inorganic oxide such as alumina or zirconia, promoted with metal such as iron, tin, tungsten, optionally in combination with a Group I or II metal such as Na, K, Rb, Cs, Mg, Ca, Sr, and Ba; rhenium in oxide or metallic form deposited on a neutral or weakly acidic support which has been additionally impregnated with an alkali metal hydroxide or stannate and subsequently reduced with hydrogen at elevated temperatures; and platinum deposited on aluminosilicate MFI zeolite. Any of these known catalysts can be used for the dehydrocyclization step. In particular embodiments, the dehydrocyclization catalyst includes, for example, chromium-oxide treated alumina, platinum- and tin-containing zeolites and alumina, cobalt- and molybdenum-containing alumina, etc. In a specific embodiment, the dehydrocyclization catalyst is a commercial catalyst based on chromium oxide on an alumina support.

High selectivity for p-xylene in the dehydrocyclization reaction is favored by providing a dehydrocyclization feedstock which comprises primarily 2,4,4-trimethylpentenes, 2,5-dimethylhexenes, and/or 2,5-dimethylhexadienes by appropriate selection of the dehydrocyclization catalyst (as described herein) and by appropriate selection of process conditions (e.g., process temperature, pressure, WHSV etc.). In most embodiments, the dehydrocyclization reaction is carried out below or slightly above atmospheric pressure, for example, at pressures ranging from about 1 psia to about 20 psia, or about 1 psia, about 2 psia, about 3 psia, about 4 psia, about 5 psia, about 6 psia, about 7 psia, about 8 psia, about 9 psia, about 10 psia, about 11 psia, about 12 psia, about 13 psia, about 14 psia, about 15 psia, about 16 psia, about 17 psia, about 18 psia, about 19 psia, and about 20 psia, inclusive of all ranges and subranges therebetween. In most embodiments, the dehydrocyclization is carried out at temperatures ranging from about 400° C. to about 600° C., or about 400° C., about 425° C., about 450° C., about 475° C., about 500° C., about 525° C., about 550° C., about 575° C., and about 600° C., inclusive of all ranges and subranges therebetween. In most embodiments, the dehydrocyclization is carried out at WHSV values of about 1 hr$^{-1}$, for example, about 0.51 hr$^{-1}$ about 1 hr$^{-1}$, about 1.5 hr$^{-1}$, or about 2 hr$^{-1}$, inclusive of all ranges and subranges therebetween. In most embodiments, the dehydrocyclization reaction is operated, at conversions ranging from about 20-50%, and provides a p-xylene selectivity (i.e., the percentage of xylene products which is p-xylene) greater than about 75%. In other embodiments, the p-xylene selectivity is about 75%, about 80%, about 85%, about 90%, about 95%, about 96%, about 97%, about 98%, or about 99%.

In addition, both the conversion and selectivity of the dehydrocyclization reaction for p-xylene can be enhanced by adding diluents to the feedstock, such as hydrogen, nitrogen, argon, and methane. Unreacted isobutene can also be used as an effective diluent to improve the p-xylene selectivity of the dehydrocyclization reaction, and to help suppress cracking. Accordingly, in some embodiments, the selectivity of the dimerization reaction step is improved by carrying out the dimerization under low conversion conditions, as discussed above, such, that the product from the dimerization reaction contains significant amounts of unreacted isobutene, a portion, of which can be recycled back to the dimerization reaction feedstock, and a portion of which is present in the dehydrocyclization reaction feedstock. In some embodiments, the dehydrocyclization feedstock comprises 1-100% 2,4,4-trimethylpentenes, 2,5-dimethylhexenes, and/or 2,5-dimethylhexadienes, with the balance diluent. In particular embodiments, the dehydrocyclization feedstock comprises less than about 50% 2,4,4-trimethylpentenes, 2,5-dimethylhexenes, and/or 2,5-dimethylhexadienes to reduce coking of the dehydrocyclization catalyst. For example, the dehydrocyclization feedstock can comprise about 1%, about 2%, about 5%, about 10%, about 15%, about 20%, about 25%, about 30%, about 35%, about 40%, about 45%, or about 50% 2,4,4-trimethylpentenes, 2,5-dimethylhexenes, and/or 2,5-dimethylhexadienes, inclusive of all ranges and sub-ranges therebetween.

The conversion of alkenes and alkanes into aromatic compounds is a net oxidation reaction that releases hydrogen from the aliphatic hydrocarbons. If no oxygen is present hydrogen gas is a co-product, and light alkanes such as methane and ethane are by-products. If oxygen is present the hydrogen is converted into water. The dehydrocydization step is typically carried out in the relative absence of oxygen (although trace levels of oxygen may be present due to leaks in the reactor system, and/or the feedstock for the dehydrocyclization reaction step may have trace contamination with oxygen). The hydrogen and light hydrocarbons produced as a by-product of the dehydrocyclization reaction, are themselves valuable compounds that can be removed and used for other chemical processes. The hydrogen can also react with isobutene and diisobutene to produce isobutane and isooctane which can be recycled to use as diluents for the oligomerization or as feedstock for the dehydrocyclization, forming isobutene by dehydrogenation of isobutane and p-xylene by dehydrocyclization of isooctane.

Typically, the high temperatures at which these dehydrocyclization reactions are carried out tend to coke up and deactivate the catalysts. To reuse the catalyst, the coke must be removed as frequently as every 15 minutes, usually by burning it off in the presence of air. Thus, even though the dehydrocyclization reaction itself is in most embodiments carried, out in the absence of oxygen, oxygen (and optionally hydrogen) can periodically be introduced to reactivate the catalyst.

The presence of hydrogenating metals such as nickel, platinum, and palladium in the catalyst will catalyze the hydrogenation of the coke deposits and extend catalyst life. In order to accommodate reactivation of the catalyst in a continuous process, two or more dehydrocyclization reactors can be used so that at least one dehydrocyclization reactor is operational while other dehydrocyclization reactors are taken "offline" in order to reactivate the catalyst. When multiple dehydrocyclization reactors are used, they can be connected in parallel or in series.

As discussed above, the hydrocarbon feedstocks used to form aromatic compounds in conventional petroleum refineries are typically mixtures of hydrocarbons. As a result, the p-xylene produced by petroleum refineries is mixed with other xylene isomers and other aromatics (e.g., light aromatics such as benzene and toluene, as well as ethylbenzene, etc.), requiring further separation and purification steps in order to provide suitably pure para-xylene for subsequent conversion to terephthalic acid or terephthalate esters suitable for polyester production, in a large-scale refinery, producing pure streams of p-xylene can be expensive and difficult. In contrast, the process of the present invention can provide relatively pure, renewable p-xylene at a favorable cost, for example, by oligomerizing acetic acid-derived isobutene to form diisobutene (e.g. about 95% 2,4,4-trimethylpentenes) at about 50% conversion in an oligomerization reactor containing a metal-doped zeolite catalyst (e.g., HZSM-5). A portion of the unreacted isobutene is recycled back to the oligomerization feedstock, while a remaining portion of the isobutene remains in the product stream to serve as a diluent in the subsequent dehydrocyclization reaction step. The resulting mixture of diisobutene and isobutene, and optionally additional diluent (e.g., hydrogen, nitrogen, argon, and methane) is then fed into a dehydrocyclization reactor and reacted in the presence of a dehydrocyclization catalyst to selectively form p-xylene (e.g., >95% of the xylenes is p-xylene). Hydrogen produced as a co-product of the dehydrocyclization can be recycled back to the dehydrocyclization feedstock as a diluent, or alternatively used as a reactant to produce other compounds (e.g., to hydrogenate alkenes or alkene byproducts for use as fuels or fuel additives, e.g., hydrogenating $C_8$ olefins such as isooctene to make isooctane for transportation fuels). Light alkanes in the hydrogen can be separated out before the purified hydrogen is utilized, or the impure light alkane/hydrogen mixture can be used directly in hydrogenation reactions.

The resulting high purity p-xylene can be condensed from the product stream of the dehydrocyclization reaction and converted to terephthalic acid (TPA) or terephthalate esters (TPA esters) without further purification. However, since the purity requirements for TPA or TPA esters used as monomers in preparing PET are quite high (e.g., typically requiring greater than about 99.5% purity), it may be desirable to further purify the renewable p-xylene thus prepared, by known methods such as simulated moving bed chromatography, fractional, crystallization or fractional distillation. Although such methods are used in conventional petrochemical processes for preparing high purity p-xylene, the "crude" p-xylene produced from the conventional process contains substantial amounts of impurities and undesirable xylene isomers and thus typically requires multiple purification steps to obtain the required purity level, in contrast, the "crude" p-xylene prepared as described herein (from acetic acid-derived isobutene) is substantially more pure than conventional petrochemically produced p-xylene, and requires only minimal purification, if at all, to obtain purities suitable for preparing TPA or TPA ester monomers for polyester production.

Renewably sourced p-xylene produced according to the present invention can be converted into either TPA or TPA esters in the same manner as purified p-xylene from conventional petrochemical processing, for example, by oxidation over a transition metal-containing catalyst (Ind. Eng. Chem. Res. 2000, 39, p. 3958-3997 reviews the patent literature). Dimethyl terephthalate (DMT) has been traditionally produced at higher purity than TPA, and can be used to manufacture PET as well. Examples of methods for producing TPA and DMT from conventional p-xylene that could be equally applied to the renewable p-xylene provided by the instant invention may be found, in U.S. Pat. Nos. 2,813,119; 3,513,193; 3,887,612; 3,850,981; 4,096,340; 4,241,220; 4,329,493; 4,342,876; 4,642,369; and 4,908,471.

As discussed herein, the dimerization of the acetic acid-derived isobutene to $C_8$ alkenes, and the subsequent dehydrocyclization of the $C_8$ alkenes to p-xylene can be carried out in a stepwise fashion, in which the dimerization product (comprising, e.g., 2,4,4-trimethylpentenes, 2,5-dimethylhexenes, and/or 2,5-dimethylhexadienes) is isolated and optionally purified prior to the dehydrocyclization step or is passed, directly to the dehydrocyclization reactor (or reaction zone) without an intervening isolation or purification step. Alternatively, in a second embodiment of a process for converting the acetic acid-derived isobutene 14 to p-xylene 15, by appropriate selection of reaction conditions (i.e., catalyst(s), reaction temperature and pressure, reactor design, etc.) the dimerization and dehydrocyclization reactions can be carried out essentially simultaneously, such that the isobutene 14 is effectively converted directly to p-xylene 15. In this regard, "essentially simultaneous" reaction steps could include direct conversion of the isobutene to p-xylene in a single reaction step, or rapid sequential conversion of the isobutene to an intermediate (e.g., a $C_8$ alkene or other intermediate), which under die reaction conditions is rapidly converted to p-xylene such that no intermediates are isolated (or need be isolated).

For example, it is known that isobutene may be converted directly to p-xylene using a bismuth oxide catalyst under oxidative conditions, see, e.g., Goldwasser et al., "The oxidation of isobutene to p-xylene over bismuth oxide-based catalysts", Journal of Chemical Technology and Biotechnology, vol. 28, issue 11, pp 733-739 (1978)(which is hereby incorporated by reference herein); see also, for example, U.S. Pat. No. 3,769,237 to Ondrey et al. (also incorporated by reference herein), or alternatively by reacting isobutene using conditions and catalysts used in known petrochemical processes such as the M-2 Forming process (Mobil), Cyclar process (UOP) and Aroforming process (IFP-Salutec), to form an aromatic product comprising p-xylene.

The present methods will be further illustrated by the following non-limiting examples:

EXAMPLES

Commercial zirconium hydroxide was dried at 120 degrees Celsius for more than 5 hours. A calculated amount of $Zn(NO_3)_2$ (from Sigma-Aldrich, more than 99.8 percent purity) was dissolved in water, forming a clear solution. The dried, zirconium hydroxide (which was also from Sigma-Aldrich, more than 99.8 percent purity) was then mixed with the solution by incipient wetness, in order to form wet powders impregnated with Zn. The wetted powder was then dried at 80 degrees Celsius for 4 hours, followed by calcination at 550 degrees Celsius for 3 hours, to obtain a $Zn_1Zr_8O_2$ catalyst by the incipient wetness impregnation method of the '312 application.

An acetic acid to isobutene process was conducted (as described in the '433 application) with the catalyst thus prepared in a fixed-bed stainless steel reactor having an inside diameter of 5 millimeters. 100 mg of the catalyst was packed between quartz wool beds. A thermocouple was placed in the middle of the catalyst bed to monitor the reaction temperature. Before beginning the reaction, the catalyst bed was pretreated by flowing 50 ml/minute of nitrogen at 450 degrees Celsius through the catalyst over a half hour. A 25 weight percent solution of acetic acid in water was then introduced into an evaporator at 180 degrees Celsius by means of a syringe pump, and the vaporized steam/acetic acid was carried into the reactor by a flowing nitrogen carrier gas at an acetic acid concentration in the gas phase of 1.36 weight percent and a WHSV of 0.1 grams of acetic acid per gram of catalyst per hour. Meanwhile, the product line was heated to in excess of 150 degrees Celsius before a cold trap, to avoid condensing the liquid products in the product line. A reaction temperature of 415 degrees Celsius was employed.

A Shimadzu 2400 gas chromatograph equipped with an auto sampling valve, HP-Plot Q column (30 m, 0.53 mm, 40 µm) and flame ionization detector was connected to the line between the reactor outlet and cold trap to collect and analyze the products in the effluent gas. After the cold trap, an online micro-GC (MicroGC 3000A equipped with molecular sieves 5A, plot U columns and thermal conductivity detectors) was used to analyze the product gases specifically, using nitrogen as a reference gas.

A consistent product of about 5 mol percent of methane, about 10 mol percent of acetone, about 33 mol percent of carbon dioxide and more than about 50 mol percent of the desired isobutene product was obtained; in contrast to the ethanol to isobutene process using these same $Zn_xZr_yO_z$ mixed oxide catalysts, no ethylene or propylene was produced. The catalyst showed very high stability over the full duration of the run, with no signs of observable deactivation after more than 1400 minutes of time-on-stream operation.

Examples 2 Through 10

For these additional examples of converting acetic acid to isobutene, additional $Zn_xZr_yO_z$ mixed oxide catalysts were prepared both by the incipient wetness method (IW in the tabulated results below) but also by the prior art hard template method (HT) described in the Sun et al, journal article (2011), and these were evaluated and the products analyzed using the same apparatus and method described above but under different sets of reaction conditions (as summarized, in the table below).

| Ex # | Catalyst | Zn/Zr ratio | Reaction temp (° C.) | WHSV ($g_{acetic}$/$g_{catal}$/hr) | Steam to carbon ratio | $C_{6\text{-}acetic\ acid}$ (wt %) | Acetone selectivity (mol %) | Isobutene selectivity (mol %) |
|---|---|---|---|---|---|---|---|---|
| 2 | HT | 1/15 | 450 | 0.25 | 5 | 1.3 | 30.5 | 41.7 |
| 3 | HT | 1/15 | 450 | 1.14 | 5 | 1.5 | 61.1 | 18.4 |
| 4 | IW | 1/8 | 415 | 0.1 | 5 | 1.4 | 9.8 | 52.5 |
| 5 | IW | 1/10 | 415 | 0.95 | 5 | 22.3 | 50.8 | 20.1 |
| 6 | IW | 1/10 | 450 | 0.16 | 2.5 | 18.8 | 0.7 | 50.6 |
| 7 | IW | 1/10 | 450 | 0.65 | 2.5 | 18.8 | 8.3 | 46.9 |
| 8 | IW | 1/10 | 415 | 0.16 | 2.5 | 18.8 | 5.7 | 57.2 |
| 9 | IW | 1/10 | 415 | 0.33 | 2.5 | 18.8 | 16.4 | 45.3 |
| 10 | IW | 1/10 | 415 | 0.65 | 2.5 | 18.8 | 30.5 | 35.0 |

Example 11

Isobutene was condensed to a liquid and pumped with a positive displacement pump into a fixed bed oligomerization reactor packed, with a commercial ZSM-5 catalyst (CBV 2314). The reactor was maintained at 175° C. and a pressure of 750 psig. The WHSV was 15 hr$^{-1}$. The reactor effluent stream was 10% unreacted isobutene, 60% isooctenes (primarily being 2,4,4-trimethylpentenes), 28% trimers, and 2% tetramers.

Example 12

Liquid isobutene was pumped with a positive displacement pump into a fixed-bed oligomerization reactor packed with a commercial ZSM-5 catalyst (CBV 2314). The reactor was maintained at 170° C. and a pressure of 750 psig. The WHSV of the isobutylene-rich stream was 50 hr$^{-1}$. The reactor effluent stream, was 20% unreacted isobutene, 64% isooctenes (primarily 2,4,4-trimethylpentenes), 15% trimers, and 1% tetramers.

Example 13

Isooctene from Example 12 was distilled to remove trimers and tetramers and then fed at a molar ratio of 1.3:1 mol nitrogen diluent gas to a fixed bed reactor containing a commercial chromium oxide doped alumina catalyst (BASF D-1145E ⅛"). The reaction was carried out at atmospheric pressure and a temperature of 550° C., with a WHSV of 1.1 hr$^{-1}$. The reactor product was condensed and analyzed by GC-MS. Of the xylene fraction, p-xylene was produced in greater than 80% selectivity. Analysis by method ASTM D6866-08 showed p-xylene to contain 96% biobased material.

Example 14

A 300 mL Ti Parr reactor was charged with 100 mL solution of glacial acetic acid containing hydrobromic acid (33 mM), cobalt acetate tetrahydrate (33 mM), and manganese acetate tetrahydrate (1 mM). The reactor was equipped with a thermocouple, mechanical stirrer, air sparger, condenser, pressure gauge, and pressure relief valve. The reactor was sealed and heated to 180° C. p-Xylene from Example 13 was subsequently pumped into the reactor at a pre-defined rate to initiate the reaction. The contents were stirred and air was bubbled, through the solution. A pressure of 400-450 psi was maintained in the system and these reaction conditions were maintained for 4 hours. After 4 hours, the reactor was cooled to room temperature. The resulting terephthalic acid was filtered from solution and washed with fresh glacial, acetic acid.

Example 15

2,5-dimethylhexadiene was run neat through a fixed bed reactor containing a commercial, chromium oxide doped alumina catalyst (BASF D-1145E ⅛"). The reaction was carried out at atmospheric pressure and a temperature of 500° C., with a WHSV of 1.0 hr$^{-1}$. The reactor product was condensed and analyzed by GC-MS. The reactor effluent stream, was 60% xylenes, and of the xylene fraction, p-xylene was produced in greater than 99% selectivity.

What is claimed is:

1. A process for making para-xylene, comprising converting acetic acid to isobutene in the presence of a mixed oxide catalyst comprising a formula of $Zn_xZr_yO_z$, wherein the ratio of x:y is from 1:100 to 10:1 and z is a stoichiometric integer for the mixed oxide catalyst, then converting the isobutene to a product composition including para-xylene.

2. The process according to claim 1, wherein the conversion of the isobutene to the paraxylene comprises oxidation of the isobutene.

3. The process according to claim 1, wherein the conversion of the isobutene to paraxylene comprises:
   dimerizing the isobutene in the presence of an oligomerization catalyst to form a dimerization product comprising one or more $C_8$ alkenes; and
   dehydrocyclizing at least a portion of the $C_8$ alkenes in the presence of a dehydrocyclization catalyst to form the product composition including para-xylene.

4. The process according to either of claim 2 or claim 3, wherein the product composition further comprises one or both of ortho-xylene and meta-xylene, and wherein the para-xylene is produced selectively compared to ortho-xylene and meta-xylene in the product composition.

5. The process according to claim 1, wherein the mixed oxide catalyst contains less than 0.14 percent by weight of sulfur.

6. The process according to claim 5, wherein the mixed oxide catalyst contains less than 0.01 percent by weight of sulfur.

7. The process according to claim 6, wherein the mixed oxide catalyst contains less than 0.001 percent by weight of sulfur.

8. The process according to claim 1 or any one of claims 5-7, wherein x:y is from 1:30 to 1:1.

9. The process according to claim 8, wherein x:y is from 1:20 to 1:5.

10. The process according to claim 9, wherein x:y is from 1:12 to 1:10.

11. The process according to claim 1, wherein the acetic acid is obtained at least in part by fermentation of one or more of five- and six-carbon sugars.

12. The process according to claim 1, wherein the acetic acid is obtained at least in part through an oxidative fermentation from ethanol.

13. The process according to claim 1, wherein the acetic acid is obtained at least in part by carbonylation of methanol.

14. The process according to claim 13, wherein the methanol is obtained at least in part by combining carbon dioxide generated from biomass and hydrogen.

\* \* \* \* \*